United States Patent [19]
Ishiguro et al.

[11] Patent Number: 4,906,790
[45] Date of Patent: Mar. 6, 1990

[54] METHOD OF OXIDIZING SECONDARY ALKYL SUBSTITUTED NAPHTALENES AND A PROCESS OF PRODUCING ISOPROPYLNAPHTHOLS

[75] Inventors: Masaharu Ishiguro, Otake; Hisaya Miki; Nobuya Hirokane, both of Iwakuni, all of Japan

[73] Assignee: Mitsui Petrochemical Industries, Ltd., Tokyo, Japan

[21] Appl. No.: 242,163

[22] Filed: Sep. 9, 1988

[30] Foreign Application Priority Data

Sep. 12, 1987 [JP] Japan .................................. 62-229239
Sep. 16, 1987 [JP] Japan .................................. 62-231490
Sep. 16, 1987 [JP] Japan .................................. 62-231489

[51] Int. Cl.$^4$ ..................... C07C 37/08; C07C 179/02
[52] U.S. Cl. .................................... 568/741; 568/565; 568/573; 568/736
[58] Field of Search ................ 568/741, 736, 573, 565

[56] References Cited

U.S. PATENT DOCUMENTS 4,503,262 3/1985 Gupton et al. ....................... 568/573
4,783,557 11/1988 Haneda et al. ....................... 568/741

FOREIGN PATENT DOCUMENTS 1093156 5/1986 Japan .................................... 568/573
3030438 2/1988 Japan .................................... 568/741

Primary Examiner—Werren B. Lone
Attorney, Agent, or Firm—Sherman and Shalloway

[57] ABSTRACT

A method of oxidizing secondary alkyl substituted naphthalenes with molecular oxygen in a liquid phase to hydroperoxides, carbinols or mixtures of these, which comprises: oxidizing the secondary alkyl substituted naphthalenes in the presence of an aromatic hydrocarbon having a fused ring which contains at least one methylene group therein in amounts of not more than about 1000 ppm based on the secondary alkyl substituted napththalene used.

A process of producing isopropylnaphthols is also disclosed, which comprises: oxidizing diisopropylnaphthalenes with molecular oxygen in a liquid phase to diisopropylnaphthalene monohydroperoxides in the presence of (a) either an aromatic hydrocarbon having a fused ring which contains at least one methylene group therein, or a palladium catalyst soluble in the reaction mixture, and (b) an organic polar compound such as acetonitrile; and then acid-decomposing the diisopropylnaphthalene monohydroperoxide to the isopropylnaphthol.

33 Claims, No Drawings

METHOD OF OXIDIZING SECONDARY ALKYL SUBSTITUTED NAPHTALENES AND A PROCESS OF PRODUCING ISOPROPYLNAPHTHOLS

This invention relates to a method of oxidizing secondary alkyl substituted naphthalenes and a process of producing isopropylnaphthols.

More particularly, the invention relates to a method of producing naphthalene hydroperoxides and/or carbinols in high yields by oxidizing secondary alkyl substituted naphthalenes with molecular oxygen in a liquid phase. The invention further relates to a process of producing isopropylnaphthols by oxidizing diisopropylnaphthalenes with molecular oxygen in a liquid phase to diisopropylnaphthalene monohydroperoxides and then by acid-decomposing the monohydroperoxide to isopropylnaphthols in high selectivities and in high yields.

It is already known that dihydroxynaphthalenes are produced by the oxidation of secondary alkyl substituted naphthalenes such as diisopropylnaphthalenes to diisopropylnaphthalene dihydroperoxides, and the subsequent acid-decomposition of the diisopropylnaphthalene dihydroperoxide with an acid catalyst. Further, the diisopropylnaphthalene dicarbinols by-produced in the oxidation of diisopropylnaphthalenes are converted to diisopropylnaphthalene dihydroperoxides by the oxidation with hydrogen peroxide. The dihydroxynaphthalenes are useful as raw materials for the production of synthetic resins, synthetic fibers, medicines, agricultural chemicals or dyestuffs, as is well known.

In U.S. Pat. No. 2,751,418 there is described a process of the catalytic oxidation of secondary alkyl substituted aromatic hydrocarbons with molecular oxygen to hydroperoxides in the presence of a noble metal catalyst such as palladium, platinum, osmium, iridium, ruthenium or rhodium. The nobel metal catalyst therein is used in a finely divided form, and the metal is, for example, supported on a solid carrier material such as alumina, or the metal is used in a colloidal form such as colloidal palladium. This type of solid or heterogeneous catalyst is disadvantageous from the standpoint of industrial feasibility of the process. Further, in the U.S. Pat. No. 2,751,418, the oxidation of alkylbenzenes such as p-cymene or sec-butylbenzene is specifically disclosed, however, nothing is described about the oxidation of secondary alkyl substituted naphthalenes such as diisopropylnaphthalenes. As another aspect of the process disclosed therein, the oxidation reaction is carried out in the presence of a weak base such as sodium hydrogen carbonate or sodium carbonate, and thus only at low pH ranges.

In U.S. Pat. No. 4,503,262 there is described that diisopropylnaphthalenes are oxidized with molecular oxygen to diisopropylnaphthalene dihydroperoxides in organic solvents in the presence of heavy metal catalysts such as organic acid salts of cobalt, and that the use of aliphatic hydrocarbons of 5–14 carbons as a solvent improves the oxidation rate, and the yield and purity of the obtained dihydroperoxides. However, the improvement is limited and has been found insufficient.

A further method of the catalytic oxidation of secondary alkyl substituted aromatic hydrocarbons with molecular oxygen to hydroperoxides is also known, in which the reaction is carried out in a reaction vessel having an inner surface coated with copper, silver or gold, to improve the oxidation rate, as is disclosed in British Pat. No. 714,545. However, in this reference also, the oxidation of alkylbenzenes such as cumene or sec-butylbenzene is specifically disclosed, but nothing is described about the oxidation of secondary alkyl substituted naphthalenes such as diisopropylnaphthalenes. A still further method is disclosed in British Pat. No. 760,367, in which cumene is oxidized in the presence of copper acetate or silver acetate to hydroperoxides. But the improvement in these methods has been still insufficient.

The present inventors have studied the application of the above-mentioned prior processes to the oxidation of secondary alkyl substituted naphthalenes, and found that in any prior process the oxidation of secondary alkyl substituted naphthalenes does not proceed at a feasible rate.

The inventors have made intensive investigations to solve the problems as mentioned above, and found that the oxidation of secondary alkyl substituted naphthalenes with molecular oxygen in a liquid phase in the presence of an aromatic hydrocarbon which has a ring fused thereto containing at least one methylene group therein provides desired hydroperoxides and/or carbinols in higher selectivities and in higher yields than in any known process.

Therefore, it is an object of the invention to provide a novel process of oxidizing secondary alkyl substituted naphthalenes with molecular oxygen in a liquid phase to hydroperoxides and/or carbinols in higher selectivities and in higher yields than in the prior arts.

Meanwhile, it is also known that diisopropylnaphthalenes such as 2,6-diisopropylnaphthalene is oxidized to 2-isopropyl-6-(2-hydroperoxy-2-propyl)naphthalene, which is in turn acid-decomposed with an acid catalyst, to provide 6-isopropyl-2-naphthol, which finds wide applications as raw materials for the production of synthetic resins, synthetic fibers, medicines, agricultural chemicals or dyestuffs, as is well known.

As hereinbefore described, the oxidation of 2,6-diisopropylnaphthalene to 2,6-diisopropylnaphthalene dihydroperoxide is already known in U.S. Pat. No. 4,503,262. In the application of this process to the selective production of the 2-isopropyl-6-(2-hydroperoxy-2-propyl)naphthalene, a monohydroperoxide, the reaction must be stopped at an initial stage, so that the conversion of the starting material and the yield of the desired monohydroperoxide are very low as well as much quantity of the raw material must be recovered.

Furthermore, the oxidation of diisopropylnaphthalenes proceeds stepwise similarly to the oxidation of diisopropylbenzenes as is already known, and accordingly it is very difficult to recover the monohydroperoxide in high yields from the reaction mixture.

A further process is already known, as is described in J. Am. Chem. Soc., 84, 284–292 (1962), in which β-isopropylnaphthalene is sulfonated at the 6-position with excess amounts of concentrated sulfuric acid to provide 2-isopropyl-6-naphthalenesulfonic acid, which is then hydrolyzed with large excess amounts of a potassium hydroxide solution, thereby to provide 6-isopropyl-2-naphthol. As will be apparent, the process needs large quantity of acids and alkalis, and is inevitably attended by a serious problem of waste water treating when being utilized in the commercial production of 6-isopropyl-2-naphthol.

A still further process is known, as is described in Japanese Patent Laid-Open No. 61-100558, in which the oxidation of diisopropylnaphthalenes is carried out in the presence of organic solvents such as chlorobenzene.

However, the yield of the monohydroperoxide in the middle of the reaction is unsatisfactorily about 40 mole % based on the diisopropylnaphthalene used.

The oxidation of β-isopropylnaphthalene, a homologue of diisopropylnaphthalenes, with molecular oxygen in the presence of an aqueous alkaline solution to β-isopropylnaphthalene hydroperoxide is disclosed in Japanese Patent Laid-Open No. 51-34138 and British Pat. No. 654,035. However, the oxidation of diisopropylnaphthalenes with molecular oxygen needs severer reaction conditions than in the oxidation of, for example, β-isopropylnaphthalene. When such severer reaction conditions are employed, the production of undesired naphthoquinones which inhibit the oxidation reaction increases, and therefore, it is infeasible to employ the oxidation process of β-isopropylnaphthalene as it is for the oxidation of diisopropylnaphthalenes.

It is also known that diisopropylbenzenes are oxidized to diisopropylbenzene dihydroperoxides, and the dihydroperoxide is decomposed in the presence of an acid catalyst to hydroquinone or resorcinol. However, the diisopropylnaphthalenes are different in the reactivity from p- or m-diisopropylbenzene, so that it is almost impossible to determine optimum reaction conditions of the oxidation of diisopropylnaphthalenes and the subsequent acid decomposition conditions on the ground of the known oxidation process of the diisopropylbenzenes.

The present inventors have, therefore, made intensive investigations of processes of oxidizing diisopropylnaphthalenes to diisopropylnaphthalene monohydroperoxides, and the acid decomposition thereof to isopropylnaphthols in particular, and found that the oxidation of diisopropylnaphthalenes with molecular oxygen in the presence of an organic polar compound such as acetonitrile, and either an aromatic hydrocarbon having a fused ring which contains at least one methylene group therein or a palladium catalyst soluble in the reaction mixture remarkably improves the selectivity and the yield of the desired diisopropylnaphthalene monohydroperoxide.

Therefore, it is another object of the invention to provide a process for producing isopropylnaphthols via diisopropylnaphthalene monohydroperoxides in high selectivities in high yields.

According to the invention, there is provided a method of oxidizing secondary alkyl substituted naphthalenes with molecular oxygen in a liquid phase to hydroperoxides, carbinols or mixtures of these, which comprises: oxidizing the secondary alkyl substituted naphthalene in the presence of an aromatic hydrocarbon having a fused ring which contains at least one methylene group therein amounts of not more than about 1000 ppm based on the secondary alkyl substituted naphthalene used.

In the method of the invention, the secondary alkyl substituted naphthalene has one or more secondary alkyls preferably of 3 or 4 carbons, and is exemplified by β-isopropylnaphthalene, β-sec-butylnaphthalene, 2,6-diisopropylnaphthalene, 2,7-diisopropylnaphthalene, 2,4-diisopropylnaphthalene, 2,6-di(sec-butyl)naphthalene or 1,7-di(sec-butyl)naphthalene, among which are preferred isopropylnaphthalenes or diisopropylnaphthalenes, and most preferred is 2,6-diisopropylnaphthalene.

A base may be or may not be used in the method of the invention, however, it is usually preferred that the reaction be carried out in the presence of a base. The base used may be any alkali metal compound known in the art as usable, such as hydroxides, carbonates, phosphates and acetates, e.g., sodium hydroxide, potassium hydroxide, sodium carbonate, potassium carbonate, potassium phosphate, sodium acetate or potassium acetate. The alkali metal compound is used usually as an aqueous solution in the reaction. The alkali metal compound may be used as a mixture.

Alkaline earth metal compounds are also usable as a base, which include calcium hydroxide, magnesium hydroxide and strontium hydroxide, among these is preferred calcium hydroxide. The alkaline earth metal compound may be used singly or as a mixture with another alkaline earth metal compound or an alkali metal compound.

In the oxidation reaction, the secondary alkyl substituted naphthalene, their oxidation products and the aqueous alkaline solution are fully emulsified usually with aid of an effective agitation, however, an emulsifier known in the art such as stearic acid may be used, if desired.

The concentration of the alkali or alkaline earth metal compound in an aqueous solution is preferably not more than about 20% by weight. The aqueous alkaline solution is used in the reaction in amounts of about 5–80% by weight, preferably in amounts of about 20–70% by weight, based on the reaction mixture. When the amount of the solution is less than about 5% by weight based on the reaction mixture, an organic mixture of the unreacted secondary alkyl substituted naphthalenes and the oxidation products thereof is poorly dispersible in the aqueous alkaline solution, to render the mixture insufficiently emulsified, and this adversely affects the oxidation reaction. When the amount of the aqueous alakline solution is more than about 80% by weight, too, the reaction mixture is insufficiently emulsified. The aqueous alkaline solution is maintained usually at a pH of not less than about 7, preferably a pH of not less than about 12 in the oxidation reaction.

The oxidation reaction is carried out in the presence of an aromatic hydrocarbon having a fused ring which contains at least one methylene group therein, which will be hereinafter often referred to as the methylene containing aromatic hydrocarbon. The aromatic hydrocarbon is composed preferably of 9–14 carbons, and is exemplified by an indane structure aromatic hydrocarbon which includes indene, indane and fluorene, and tetralin structure aromatic hydrocarbon which includes tetralin, 9,10-dihydrophenanthrene and 9,10-dihydroanthracene. The methylene containing aromatic hydrocarbon may be used singly or as a mixture of two or more. Tetralin, 9,10-dihydroanthracene or fluorene is particularly preferred in the invention.

The aromatic hydrocarbon is used in amounts of not more than about 1000 ppm, preferably of about 5–1000 ppm, most preferably of about 10–500 ppm, based on the secondary alkyl substituted naphthalene used. When the aromatic hydrocarbon is used in amounts of more than about 1000 ppm based on the secondary alkyl substituted naphthalene used, the oxidation of the aromatic hydrocarbon undesirably predominates over the oxidation of the secondary alkyl substituted naphthalene used, whereas when the aromatic hydrocarbon is used in amounts of less than about 5 ppm, substantially no improvement is attained in the selectivity of the reaction and the yield of the desired products.

The aromatic hydrocarbon may be either added as it is to the reaction mixture at the outset of the reaction, or added as it is continuously and gradually in portions during the reaction or as a solution in an organic solvent inactive to the oxidation reaction such as n-decane.

In the oxidation reaction of the invention, it is preferred that the reaction be carried out in the presence of a catalyst composed of a palladium compound which is soluble in the reaction mixture. The preferably used catalyst includes inorganic palladium compounds such as palladium chloride, palladium sulfate, palladium nitrate, sodium tetrachloropalladate(II), ammonium tetrachloropalladate(II), and organic palladium compounds such as palladium acetylacetonate, palladium oxalate or palladium acetate, and among these are particularly preferred palladium chloride, palladium nitrate or palladium acetate. The palladium catalyst is used in the reaction in amounts of not less than about 0.5 ppm as metallic palladium based on the secondary alkyl substituted naphthalene used.

Herein the specification, the reaction mixture means a solution of a mixture of the unreacted secondary alkyl substituted naphthalene, if any, oxidation products thereof, i.e., hydroperoxides and/or carbinols, the base and water. Namely, the reaction mixture means a solution of a mixture present at any instant throughout the oxidation reaction of the secondary alkyl substituted naphthalene used. Therefore, when the reaction system contains no insolubles, the entire of the reaction system is a reaction mixture.

More specifically, when an aqueous alkaline solution is used in the reaction, the reaction mixture is composed of two phases a water-immiscible or insoluble organic phase and an aqueous phase. The palladium catalyst used is at the outset of the reaction dissolved in amounts of not less than about 5 ppm based on the secondary alkyl substituted naphthalene used in the reaction mixture as hereinbefore described, and in this case, the palladium catalyst may be dissolved either in the water-immiscible organic phase or in the aqueous phase, or in both phases, in total in amounts of not less than about 5 ppm based on the secondary alkyl substituted naphthalene used.

Meanwhile, when a powdery base is used, not as an aqueous solution thereof, the reaction mixture is composed only of an organic phase. In this case, a palladium catalyst soluble in the organic phase is used, such as palladium acetylacetonate.

When the reaction is carried out batchwise, the palladium catalyst is dissolved in the reaction mixture in amounts of not less than about 5 ppm based on the secondary alkyl substituted naphthalene used at the outset of the reaction. When the reaction is carried out continously, the palladium catalyst is so used as to be present in amounts of not less than about 5 ppm based on the total amount of the unreacted secondary alkyl substituted naphthalene circulated to a reaction zone and the secondary alkyl substituted naphthalene anew added to the reaction zone.

In practicing the invention, it is preferred that the palladium catalyst be first added to a solvent in which the catalyst is soluble to prepare a catalyst solution of a suitable concentration, and the solution is fed into a reaction vessel together with a secondary alkyl substituted naphthalene and a base. This method assures the presence of the catalyst in amounts exactly predetermined at the outset of the reaction. However, if desired, the catalyst solution may be added to the reaction mixture continously or intermittently in small portions after the reaction has started. In this case, an aqueous alkaline solution of the catalyst is preferably used.

In the invention, the solvent used for the preparation of the palladium catalyst solution may be water, aqueous alkaline solutions, aqueous acidic solutions or hydrocarbons, and more specifically, the solvent is selected depending upon the palladium compound used as a catalyst. For instance, when palladium chloride is used as a catalyst, an aqueous acidic or alkaline solution is preferred as a solvent, since palladium chloride is scarcely soluble in neutral water. The aqueous acidic or alkaline solution may be, for example, hydrochloric acid or sodium hydroxide solution, respectively. When palladium sulfate is used as a catalyst, either almost neutral water, an aqueous acidic solution or an alkaline solution may be used as a solvent. When an organopalladium compound such as palladium acetylacetonate is used as a catalyst, since an organopalladium compound is usually soluble in hydrocarbons such as alkylbenzenes or secondary alkyl substituted naphthalenes, such hydrocarbons are preferably used as a solvent.

The concentration of a palladium compound in the catalyst solution thus prepared is not specifically limited in the invention, so far as the concentration of the catalyst in the reaction mixture is maintained as being not less than about 0.5 ppm as metallic palladium based on the secondary alkyl substituted naphthalene used. However, it is advantageous to use a solution which contains a palladium compound in concentrations of about 10–1000 ppm as metallic palladium since the concentration of the palladium catalyst in the reaction mixture is readily adjusted to not less than about 0.5 ppm as metallic palladium based on the secondary alkyl substituted naphthalene used when such a catalyst solution is used.

The process in accordance with the invention uses a homogeneous palladium catalyst, or a catalyst dissolved in the reaction mixture in the reaction, and thus the process has an advantage in that a high oxidation reaction rate is achieved in the presence of only a very small amount of a catalyst. On the contrary, according to a prior process in which a heterogeneous catalyst, or metallic palladium or palladium supported on a solid carrier material dispersed in the reaction mixture is used, the oxidation rate is usually slow, and it is therefore necessary to use much amounts of a palladium catalyst to increase the reaction rate.

It is preferred that the oxidation reaction of the invention be effected in the presence of a palladium catalyst in amounts of not less than about 0.5 ppm as metallic palladium based on the secondary alkyl substituted naphthalene used, as hereinbefore described, since when the catalyst amount is less than about 0.5 ppm as metallic palladium based on the secondary alkyl substituted naphthalene used, the oxidation rate is not scarcely improved. From the industrial standpoint, the use of a palladium catalyst in amounts of not less than about 2 ppm is preferred. An upper limit is not specically limited, but the amount of the catalyst used is usually up to about 1000 ppm as metallic palladium based on the secondary alkyl substituted naphthalene used from the standpoint of process economy.

Further the pH of the reaction mixture is preferably not less than about 7. The pH of the reaction mixture may be measured as follows. An amount of 10–20 ml of the reaction mixture is sampled and left standing, and the pH of the resulting aqueous phase is directly measured. When a difficulty is attended in the separation of the aqueous phase from the organic phase, methyl isobutyl ketone saturated with water is added to the sampled reaction mixture, and the pH of the solution can be measured. In the process of the invention, it is especially preferred that the pH of the reaction mixture be not less than about 12 to remarkably increase the oxidation rate. In this regard, the use of a strong base such as sodium hydroxide rather than a weak base such as sodium carbonate is preferred in the invention.

However, the reaction may be carried out at a pH of less than about 12 in the presence of a weak base such as sodium carbonate. When this method is employed, it is preferred that a palladium compound be used usually in amounts of not less than about 50 ppm as metallic palladium based on the secondary alkyl substituted naphthalene used, to attain an oxidation rate substantially the same as in the reaction at a high pH region.

In the process of the invention, molecular oxygen is used as an oxidant, and usually air is used. Although the amount of the molecular oxygen used is not specifically limited, it is usually in the range of about 5–15 Nl/hour as air in relation to 100 g of the secondary alkyl substituted naphthalene used.

The process of the invention may be carried out either batchwise or in a continuous manner. The reaction is effected usually at temperatures ranging from about 80° C. to about 150° C., preferably from about 90° C. to about 130° C., usually for a period of about 6–40 hours, although depending upon the other reaction conditions such as reaction temperatures. The reaction is usually carried out under elevated pressures, but may be carried out under normal or reduced pressures, if necessary.

In the process of the invention, the use of reaction initiator is preferred. The reaction initiator used includes, for example, an azobis initiator such as α, α-azobis(cyclohexane-1-carbonitrile), or a hydroperoxide as an oxidation product of naphthalenes or their derivatives. The amount of the reaction initiator used is usually in the range of about 0.005–1 parts by weight per 100 parts by weight of the reaction mixture fed.

According to the process of the invention, the secondary alkyl substituted naphthalene is oxidized to provide hydroperoxides and/or carbinols. When 2,6-diisopropylnaphthalene is used as a starting material, there are produced hydroperoxides which include 2,6-bis(2-hydroperoxy-2-propyl)naphthalene (referred to also as 2,6-diisopropylnaphthalene dihydroperoxide), 2-(2-hydroxy-2-propyl)-6-(2-hydroperoxy-2-propyl)naphthalene and 2-isopropyl-6-(2-hydroperoxy-2-propyl)-naphthalene, and/or carbinols which include 2,6-bis(2-hydroxy-2-propyl)naphthalene and 2-isopropyl-6-(2-hydroxy-2-propyl)naphthalene.

The composition of the reaction products may be determined by liquid chromatography. By way of example, an alcohol is added to the reaction mixture, and the resultant solution is subjected to chromatographic analysis to determine the composition of the products qualitatively.

After the reaction, the reaction mixture, if necessary after the addition thereto of, for example, methyl isobutyl ketone, is separated into an aqueous layer and an organic oily layer, in which the hydroperoxides and/or carbinols produced are contained. Thus, the total amount of the hydroperoxides produced in the reaction may be determined by the iodometric analysis of the organic layer. The removal of solvents from the reaction mixture provides a material which gives dihydroxynaphthalenes by acid decomposition.

As set forth above, according to the process of the invention, not only a high oxidation rate but also a high yield of the desired oxidation products of the secondary alkyl substituted naphthalene used, that is, hydroperoxides and carbinols, are achieved. In particular, both of the alkyls of the secondary alkyl substituted naphthalene are oxidized in the oxidation. The use of a palladium catalyst remarkably enhances the oxidation rate.

As a further aspect of the invention, there is provided a process of producing isopropylnaphthols.

A first process of producing isopropylnaphthol according to the invention comprises:

oxidizing diisopropylnaphthalenes with molecular oxygen in a liquid phase to diisopropylnaphthalene monohydroperoxides in the presence of (a) an organic polar compound in amounts of about 0.001–10 parts by weight per one part by weight of the diisopropylnaphthalene and (b) an aromatic hydrocarbon having a fused ring which contains at least one methylene group therein in amounts of from about $10^{-4}$ parts by weight to about 0.005 parts by weight per one part by weight of the diisopropylnaphthalene used; and then, acid-decomposing the diisopropylnaphthalene monohydroperoxide to the isopropylnaphthol.

Diisopropylnaphthalenes used include, for example, 2,6-diisopropylnaphthalene, 2,7-diisopropylnaphthalene and 1,4-diisopropylnaphthalene, among which 2,6-diisopropylnaphthalene is particulary preferred.

According to the process of the invention, the oxidation of the diisopropylnaphthalene is carried out by blowing a gas containing molecular oxygen into an emulsified mixture of diisopropylnaphthalenes, an aqueous alkaline solution, a methylene containing aromatic hydrocarbon and an organic polar compound under an effective mechanical agitaton, substantially in the same as in the oxidation of seconary alkyl substituted naphthalenes hereinbefore described.

In this oxidation of diisopropylnaphthalenes, the aqueous alkaline solution is not necessarily used, however, it is preferred that the oxidation be effected at a pH ranging from about 3 to about 11, preferably from about 4 to about 9, in the presence of the alkaline solution.

The alkali used may be the same as previously described, and may be any alkali metal compound or alkaline earth metal compound known in the art as usable, such as hydroxides, carbonates, phosphates and acetates, e.g., sodium hydroxide, potassium hydroxide, sodium carbonate, potassium carbonate, potassium phosphate, sodium acetate, potassium acetate, calcium hydroxide, magnesium hydroxide or strontium hydroxide, among which is preferred sodium acetate, potassium acetate, potassium carbonate or sodium hydroxide. The alkali compound may be used as a mixture, and is used usually as an aqueous solution in the reaction.

The concentration of the alkali or alkaline earth metal compound in an aqueous solution is preferably not more than about 20% by weight. The aqueous alkaline solution is used in the reaction in amounts of about 5–80% by weight, preferably in amounts of about 20–70% by weight, based on the reaction mixture, similarly in the oxidation of secondary alkyl substituted naphthalenes hereinbefore described.

The methylene group containing aromatic compound used is the same as hereinbefore described, however it is used in amounts ranging from about $10^{-4}$ parts by weight to about 0.005 parts by weight, preferably $5 \times 10^{-4}$ parts by weight to about 0.003 parts by weight, per one part by weight of the diisopropylnaphthalene used. When the aromatic hydrocarbon is used in amounts of more than about 0.005 parts by weight per one part by weight of the diisopropylnaphthalene used, the oxidation of the aromatic hydrocarbon undesirably predominates over the oxidation of the diisopropylnaphthalene used, whereas when the aromatic hydrocarbon is used in amounts of less than about $10^{-4}$ parts by weight, substantially no improvement is attained in the selectivity of the reaction and the yield of the desired oxidation products.

The aromatic hydrocarbon may be either added as it is to the reaction mixture at the outset of the reaction, or added as it is continuously and gradually in portions during the reaction or as a solution in an organic solvent inactive to the oxidation reaction such as n-decane.

In the process of the invention, an organic polar compound is used. The organic polar compound used includes, for example, an aliphatic or aromatic nitrile compound, an aliphatic or aromatic nitrated compound, a chlorinated benzene, dimethylsulfoxide and sulforane. More specifically, there may be mentioned as examples of the polar compound, acetonitrile, propionitrile, valeronitrile, benzonitrile, nitromethane, nitrobenzene, dichlorobenzene, and the like. Acetonitrile is most preferred.

The organic polar compound is used in the invention in amounts of about 0.001–10 parts by weight, preferably of about 0.01–5 parts by weight, per one part by weight of the diisopropylnaphthalene used. When the amount of the organic polar compound used is less than about 0.001 parts by weight per one part by weight of the diisopropylnaphthalene used, substantially no improvement in the yield of diisopropylnaphthalene monohydroperoxide is achieved, whereas when the amount of the organic polar compound used is more than about 10 parts by weight, undesired ketone compounds are by-produced in large amounts, resulting in low yields of desired diisopropylnaphthalene monohydroperoxide.

The presence of the polar compound, in particular acetonitrile, in the oxidation reaction controls the oxidation of the diisopropylnaphthalene to desirably produce diisopropylnaphthalene monohydroperoxide in high selectivities and in high yields, so that the subsequent acid decomposition of the oxidation products provides very pure isopropylnaphthol in high yields.

In the process of the invention, molecular oxygen is used as an oxidant, and usually air is used. Although the amount of the molecular oxygen used is not specifically limited, but usually in the range of about 5–15 Nl/hour as air in relation to 100 g of the diisopropylnaphthalene used.

The process of the invention may be carried out either batchwise or in a continuous manner. The reaction is effected usually at temperatures ranging from about 80° C. to about 150° C., preferably from about 90° C. to about 130° C., usually for a period of about 6–40 hours, although depending upon the other reaction conditions such as reaction temperatures. The reaction is usually carried out under elevated pressures, but may be carried out under normal or reduced pressures, if necessary.

In the process of the invention, the use of reaction initiator is preferred. The reaction initiator used includes, for example, an azobis initiator such as α, α-azobis(cyclohexane-1-carbonitrile). The amount of the reaction initiator used is usually in the range of about 0.005–1 parts by weight per 100 parts by weight of the reaction mixture fed.

According to the process of the invention, diisopropylnaphthalenes, for example, 2,6-diisopropylnaphthalene is oxidized to 2-isopropyl-6-(2-hydroperoxy-2-propyl)naphthalene, and in addition as by-products, 2,6-diisopropylnaphthalene dihydroperoxide, 2-(2-hydroxy-2-propyl)-6-(2-hydroperoxy-2-propyl)naphthalene, 2,6-bis(2-hydroxy-2-propyl)naphthalene and 2-isopropyl-6-(2-hydroxy-2-propyl)naphthalene.

The composition of the reaction products may be determined by liquid chromatography. By way of example, after the reaction, an organic layer is separated from an aqueous layer, and the aqueous layer is extracted with ether. The ether and the organic layer are combined together, and the solution is subjected to chromatography. By the analysis the proportions of the reaction products as well as the unreacted diisopropylnaphthalenes can be determined.

After the oxidation reaction has been completed, the methylene group containing aromatic compound and organic polar compound contained in the organic layer in the resultant reaction mixture may be partially removed therefrom by, for example, distillation, when desired. Then a water-immiscible or insoluble dialkyl ketone is added to the reaction mixture to separate an organic layer from an aqueous layer.

The addition of a water-immiscible dialkyl ketone to the reaction mixture after the oxidation reaction is preferably effected so that the hydroperoxides produced, in particular, 2,6-diisopropylnaphthalene dihydroperoxide, remain dissolved in the reaction mixture after cooling the reaction mixture. More specifically, when the conversion rate has been raised to a significant degree, the resultant reaction mixture contains hydroperoxides, in particular, 2,6-diisopropylnaphthalene dihydroperoxide, in large proportions which is liquid at the reaction temperature but solidifies when the reaction mixture is cooled to room temperatures. When the hydroperoxide produced is cooled, it incorporates thereinto an alkaline water and solidifies, so that it is difficult to remove the alkaline water from the reaction mixture when the reaction mixture is cooled as it stands. Thus, the addition of a water-immiscible dialkyl ketone to the reaction mixture after the oxidation reaction makes the handling of the reaction mixture easy.

Dialkyl ketones of 5–10 carbons are preferred as the water-immiscible dialkyl ketone as above-mentioned, and there may be used, for example, methyl propyl ketone, methyl isobutyl ketone, diisopropyl ketone, ethyl isobutyl ketone, propyl butyl ketone, diisobutyl ketone or amyl butyl ketone, among these is preferred in particular methyl isobutyl ketone.

The dialkyl ketone is added in amounts of about 0.2–5 parts by weight, preferably of about 0.5–3 parts by weight, per one part by weight of the reaction mixture, and the resultant mixture is separated into an aqueous layer and an organic layer at temperatures of about 30°–90° C. The thus separated organic phase contains diisopropylnaphthalene monohydroperoxide therein.

The use of the other organic solvents such as acetone or methyl ethyl ketone, alcohols such as methanol or ethanol, aliphatic lower carboxylic acids such as acetic acid or propionic acid, or hydrocarbons such as benzene, toluene or be avoided. The use of such solvents other than the water-insoluble dialkyl ketone renders the separation of an organic layer difficult, but also allows the alkali to remain in much amounts in the resultant organic layer. When an organic layer containing large amounts of the alkali therein is used in the subsequent acid decomposition, the yield of isopropylnaphthalene from isopropylnaphthalene monohydroperoxide is low.

An aqueous alkaline solution is then further added to the organic phase and maintained again at temperatures of about 30°–90° C., to separate the resultant organic layer from the aqueous layer, to remove by-produced 2,6-diisopropylnaphthalene dihydroperoxide and the like soluble in the aqueous layer from the organic layer. This second separation of the organic layer from the aqueous layer is of significant importance to improve the purity of isopropylnaphthol obtained in the subsequent acid decomposition of the oxidation reaction products. When the second separation is omitted, dihydroxynaphthalene and the like contaminate the isopropylnaphthol obtained in the subsequent acid decomposition and reduce the purity thereof.

The alkali used in the above separation may be the same as hereinbefore described. The alkaline solution has preferably concentrations of about 5–50% by weight, more preferably about 10–30% by weight, and is added in amounts of about 5–80% by weight, preferably about 20–70% by weight based on the reaction mixture.

The alkali used in the oxidation reaction is separated into the aqueous layer in this second separation process, and the organic layer may be washed with water, if necessary, after the separation from the aqueous layer.

The addition of a water-insoluble dialkyl ketone to the reaction mixture after completion of the oxidation reaction prevents the solidification of the reaction products and allows the reaction products to remain dissolved in the reaction mixture, thus making the post-handling of the reaction mixture easy, but also remarkably reduces the amount of the alkali which otherwise gets mixed with the organic layer and deteriorates the purity of the isopropylnaphthol obtained. The amount of the alkali in the organic layer may be determined by atomic absorption spectroscopy or neutralization titration, if necessary.

In accordance with the process of the invention, the oxidation reaction product containing diisopropylnaphthalene monohydroperoxide produced is acid-decomposed in the presence of the water-insoluble dialkyl ketone, to provide a reaction mixture which contains isopropylnaphthol. It is advantageous to carry out the acid-decomposition of diisopropylnaphthalene monohydroperoxide further in the presence of acetone since a higher yield of isopropylnaphthol is attained. The acetone is used in amounts of about 0.2–2 parts by weight, preferably of about 0.5–1 parts by weight, per one part by weight of the organic layer separated.

The acid-decomposition is carried out in the presence of an acid catalyst. The acid catalyst used includes, for example, an inorganic strong acid such as sulfuric acid, hydrochloric acid or phosphoric acid; a strongly acidic ion exchange resin; a solid acid such as silica gel or silica-alumina; an organic strong acid such as haloacetic acid, e.g., chloroacetic acid, an alkanesulfonic acid, e.g., methanesulfonic acid or arenesulfonic acid, e.g., benzenesulfonic acid or p-toluenesulfonic acid; and a heteropolyacid such as phosphorous tungstic acid or phosphorous molybdicacid.

The acid catalyst is used usually in amounts of about 0.05–10% by weight based on the total of the reaction mixture, although somewhat depending upon the catalyst used and the reaction conditions. The acid-decomposition is carried out at temperatures usually of about 0°–100° C., preferably of about 20°–80° C.

The acid-decomposition may be preferably carried out in the presence of hydrogen peroxide to oxidize 2-isopropyl-6-(2-hydroxy-2-propyl)naphthalene by-produced in the oxidation reaction among the carbinols to the monohydroperoxide, which is then decomposed to isopropylnaphthol in the presence of the catalyst, to increase the yield of isopropylnaphthol. Hydrogen peroxide is added usually as an aqueous solution to the reaction mixture while the acid-decomposition is carried out. A compound which produces hydrogen peroxide in the reaction conditions may also be used, such as sodium peroxide.

In accordance with the invention, it is in particular preferred that hydrogen peroxide be used in amounts of about 0.9–2 moles, most preferably about 1.0–1.5 moles, per mole of the alcoholic hydroxyls of the aforesaid carbinols, to produce the desired isopropylnaphthol in high yields. Further, the use of hydrogen peroxide supresses effectively the condensation of the carbinols to produce undesired by-products.

After the acid decomposition, acetone is removed from the reaction mixture by distillation, and then the water-insoluble dialkyl ketone, to prepare a slurry of aliphatic hydrocarbons, from which isopropylnaphthol is recovered. The preparation of the aliphatic hydrocarbon slurry in the recovery of the isopropylnaphthol will be hereinafter described.

The isolation of isopropylnaphthol from the reaction mixture will be now more fully described. When the acid decomposition is effected in the presence of acetone, the catalyst used is removed prior to the removal of acetone. When a solid acid catalyst is used, it may be removed by filtration. When an acid catalyst which is soluble in the reaction mixture, such as sulfuric acid, is used, an alkali such as sodium hydroxide or sodium carbonate is added as an aqueous solution to the reaction mixture, to neutralize the acid catalyst to salts insoluble in an organic layer, thereby to extract the salt into an aqueous layer. Then the mixture is subjected to distillation under normal pressures or reduced pressures to remove the acetone. Some of the acetone is the reaction product in the acid decomposition and the remaining is the acetone which has been added to the reaction mixture when the acid decomposition is carried out, as previously set forth.

The mixture of the organic and aqueous phases is then separated into the aqueous layer and the organic layer. The aqueous layer separated from the organic layer contains, for example, neutralized catalyst, and usually is discarded. If necessary, for the purpose of complete removal of the neutralized catalyst, water is added to the aqueous layer, and then the resultant aqueous layer is separated.

In the process of the invention, the organic layer is distilled to remove the water-insoluble dialkyl ketone therefrom, and it is preferred that at the same time isopropylnaphthol is recovered as a slurry of aliphatic hydrocarbons. A method to form such a slurry will be described hereinafter. In the distillation of the dialkyl ketone, it may not be necessarily removed completely from the organic layer. Namely, small amounts of the dialkyl ketone may remain in the resultant slurry. The distillation of the dialkyl ketone is carried out usually under from normal pressures to reduced pressures of about 20 mmHg and at bottom temperatures of about 50°–120° C.

Some examples of methods to form the aforesaid slurry of aliphatic hydrocarbons which contains the resultant isopropylnaphthol while the dialkyl ketone is removed from the organic layer will be given. In an exemplified method, the water-insoluble dialkyl ketone is removed by distillation while an aliphatic hydrocarbon is added to the organic layer, thereby to precipitate the isopropylnaphthol in the hydrocarbon to provide a slurry. In a further method, an aliphatic hydrocarbon is first added to the organic layer, and the water-insoluble dialkyl ketone is removed by distillation from the resultant mixture, thereby to precipitate the isopropylnaphthol in the hydrocarbon to form a slurry.

The dialkyl ketone should not remain in much amounts in the organic layer when the slurry is formed. When the dialkyl ketone remains in large amounts, the yield of isopropylnaphthol is reduced, but also the purity of the isopropylnaphthol obtained is reduced. It is preferred, therefore, that isopropylnaphthol is precipitated from the organic layer which has a weight ratio of the dialkyl ketone to the aliphatic hydrocarbon of not more than about 0.15, more preferably not more than 0.1, and most preferably not more than 0.075.

There may be used an aliphatic hydrocarbon of 8–13 carbons to form the slurry, and n-octane, n-nonane, n-decane and the like, for example, are preferred as such aliphatic hydrocarbons. The aliphatic hydrocarbon is used in amounts of about 50–1000 parts by weight, preferably of about 100–300 parts by weight, per 100 parts by weight of the acid decomposition product except the water-insoluble dialkyl ketone.

The slurry is then heated to an elevated temperature to melt the solids or precipitates contained therein, and then the slurry is cooled to about room temperatures so that isopropylnaphthol crystallizes out, and the isopropylnaphthol is then filtered. However, the slurry obtained may be cooled as it is, and the isopropylnaphthol precipitates may be collected by filtration.

A second process of producing isopropylnaphthol in accordance with the invention comprises:

oxidizing diisopropylnaphthalenes with molecular oxygen in a liquid phase to diisopropylnaphthalene monohydroperoxides in the presence of (a) an organic polar compound in amounts of about 0.001–10 parts by weight per one part by weight of the diisopropylnaphthalene used and (b) a palladium catalyst soluble in a reaction mixture in amounts of not less than about 0.1 ppm, preferably not less than about 0.5 ppm, as metallic palladium, based on the diisopropylnaphthalene used; and then, acid-decomposing the diisopropylnaphthalene monohydroperoxide to the isopropylnaphthol.

In the second process, a palladium catalyst soluble in the reaction mixture is used in place of the methylene containing aromatic compound, and otherwise in the same manner as in the first process, the oxidation of diisopropylnaphthalenes is carried out. Therefore, the oxidation is carried out preferably in the presence of an aqueous alkaline solution as well as an organic polar compound and a palladium catalyst, wherein the aqueous alkaline solution and the organic polar compound may be the same as before described, under an effective mechanical agitation so that the reaction mixture forms an emulsion, while air is blown into the emulsion.

The catalyst used is a palladium compound which is soluble in the reaction mixture of which definition is provided hereinbefore, and the palladium compound usable includes, for example, inorganic palladium compounds such as palladium chloride, palladium sulfate, palladium nitrate, sodium tetrachloropalladate(II), ammonium tetrachloropalladate(II), and organic palladium compounds such as palladium acetylacetonate, palladium oxalate or palladium acetate, and among these are particularly preferred palladium chloride, palladium nitrate or palladium acetate.

The palladium catalyst is used in the reaction in amounts of not less than about 0.1 ppm, preferably not less than about 0.5 ppm, and most preferably in amounts of about 10–50 ppm, as metallic palladium, based on the diisopropylnaphthalene used. The manner in which the catalyst is used in the reaction is described hereinbefore.

The acid decomposition of the oxidation products is effected in the same manner as in the first process.

As set forth above, according to the process for the production of the isopropylnaphthols of the invention, the oxidation of diisopropylnaphthalene is carried out in the presence of a specific organic polar compound and, either a methylene containing aromatic compound or a palladium catalyst soluble in the reaction mixture, so that the diisopropylnaphthalene monohydroperoxide is produced in a high selectivity and in a high yield, and thus the acid decomposition of the oxidation products produces isopropylnaphthol in a very high yield.

The invention will now be more fully described with reference to examples, which however are not to be construed as limiting to the invention.

EXAMPLE 1

In a 500 ml capacity autoclave made from SUS 21L provided with a stirrer, a cooling tube, a sampling opening, an inlet tube and a thermowell were placed 50.0 g of 2,6-diisopropylnaphthalene, 100.0 g of a 4.5% aqueous sodium hydroxide solution, 10.0 g of a 1% aqueous sulfuric solution of $PdCl_2$ (1200 ppm based on palladium of 2,6-diisopropylnaphthalene), 0.05 g of 9,10-dihydroanthracene (1000 ppm based on 2,6-diisopropylnaphthalene) and 0.20 g of an initiator (azobiscyclohexanecarbonitrile). The autoclave was heated to 100° C. in an oil bath, and was pressurized to 5 kg/cm$^2$G with air, and then the oxidation was carried out under the pressure for 12 hours while air was fed thereinto at a rate of 20 liters per hour.

After the completion of the reaction, 50.0 g of methyl isobutyl ketone was added to the reaction mixture to separate an organic layer from an aqueous layer. The organic layer was diluted with methanol and analyzed by liquid chromatography. The results are shown in Table 1.

COMPARATIVE EXAMPLE 1

Palladium chloride and 9,10-dihydroanthracene were not used and otherwise in the same manner as in Example 1, the reaction was carried out for 12 hours. The results are shown in Table 1.

EXAMPLE 2

Palladium chloride was not used and otherwise in the same manner as in Example 1, the reaction was carried out for 12 hours. The results are shown in Table 1.

COMPARATIVE EXAMPLE 2

9,10-Dihydroanthracene was not used and otherwise in the same manner as in Example 1, the reaction was carried out for 12 hours. The results are shown in Table 1.

EXAMPLE 3

An amount of 100.0 g of a 4.5% aqueous potassium hydroxide solution was used in place of the sodium hydroxide solution, and otherwise in the same manner as in Example 1, the reaction was carried out for 12 hours. The results are shown in Table 1.

EXAMPLE 4

An amount of 10.0 g of a 1% aqueous sulfuric acid solution of $Pd(NO_3)_2$ was used (920 ppm as palladium based on 2,6-diisopropylnaphthalene) in place of the $PdCl_2$ solution, and otherwise in the same manner as in Example 1, the reaction was carried out for 12 hours. The results are shown in Table 1.

EXAMPLE 5

TABLE 1

| | Conversion of 2,6-Diisopropylnaphthalene (mole %) | Yield of Reaction Product (mole %) | | | | |
|---|---|---|---|---|---|---|
| | | $DHP^1$ | $HHP^2$ | $DCA^3$ | $MHP^4$ | $MCA^5$ |
| Example 1 | 99.5 | 25.5 | 32.0 | 13.6 | 5.5 | 5.3 |
| Comparative 1 | 93.2 | 16.3 | 27.0 | 12.5 | 8.5 | 8.0 |
| Example 2 | 98.0 | 20.3 | 29.9 | 15.3 | 7.3 | 7.0 |
| Comparative 1 | 96.3 | 18.9 | 29.0 | 13.6 | 8.6 | 9.2 |
| Example 3 | 99.7 | 25.7 | 37.2 | 11.3 | 7.3 | 6.5 |
| Example 4 | 99.8 | 27.0 | 36.1 | 11.5 | 5.3 | 4.9 |
| Example 5 | 99.2 | 21.9 | 30.5 | 12.0 | 9.0 | 7.6 |
| Example 6 | 99.4 | 23.7 | 30.6 | 12.9 | 7.6 | 7.0 |
| Example 7 | 98.6 | 23.8 | 30.5 | 13.8 | 6.0 | 5.7 |

Notes:
[1]DHP: 2,6-diisopropylnaphthalene dihydroperoxide;
[2]HHP: 2-(2-hydroxy-2-propyl)-6-(2-hydroperoxy-2-propyl)naphthalene;
[3]DCA: 2,6-bis(2-hydroxy-2-propyl)naphthalene;
[4]MHP: 2-isopropyl-6-(2-hydroperoxy-2-propyl)naphthalene;
[5]MCA: 2-isopropyl-6-(2-hydroxy-2-propyl)naphthalene An amount of 0.05 g of tetralin was used in place of 9,10-dihydroanthracene and otherwise in the same manner as in Example 1, the reaction was carried out for 12 hours. The results are shown in Table 1.

EXAMPLE 6

Palladium chloride was used in amounts of 3 ppm based on the diisopropylnaphthalene and otherwise in the same manner as in Example 1, the reaction was carried out for 12 hours. The results are shown in Table 1.

EXAMPLE 7

An amount of 0.05 g of fluorene was used in place of 9,10-dihydroanthracene and otherwise in the same manner as in Example 1, the reaction was carried out for 12 hours. The results are shown in Table 1.

EXAMPLE 8

In a 500 ml capacity autoclave made from SUS 21L provided with a stirrer, a cooling tube, a sampling opening, an inlet tube and a thermowell were placed 50.0 g of 2,6-diisopropylnaphthalene, 100.0 g of a 4.5% aqueous potassium acetate solution, 10.0 g of acetonitrile (0.2 parts by weight per one part by weight of 2,6-diisopropylnaphthalene), 0.05 g of 9,10-dihydroanthracene (1000 ppm based on 2,6-diisopropylnaphthalene) and 0.20 g of an initiator (azobiscyclohexanecarbonitrile). The autoclave was heated to 100° C. in an oil bath, and was pressurized to 5 kg/cm$^2$G with air, and then the oxidation was carried out under the pressure for 12 hours while air was fed thereinto at a rate of 20 liters per hour.

After the completion of the reaction, 50.0 g of methyl isobutyl ketone was added to the reaction mixture to separate an organic layer from an aqueous layer which was found to have a pH of 3.8. The organic layer was diluted with methanol and analyzed by liquid chromatography. The results are shown in Table 2.

The organic layer was mixed with 50.0 g of a 10% sodium hydroxide solution and an organic layer was separated again. Water and methyl isobutyl ketone were removed from the organic layer with a rotary evaporator, and there was added to the residue methyl isobutyl ketone anew in amounts equal to the removed water and methyl isobutyl ketone. The resultant solution was fed together with acetone into a three necked 500 ml capacity Pyrex (registered trademark) flask containing diluted sulfuric acid over 3 hours at reflux temperatures, while simultaneously an acetone-diluted 60% hydrogen peroxide aqueous solution was fed into the flask over 3 hours. After the addition, the reaction was carried out for another 2 hours.

After the completion of the reaction, the reaction mixture was neutralized with a diluted aqueous sodium hydroxide solution, and then acetone and water were removed therefrom. Then an amount of 50 g of n-octane was added to the reaction mixture, and the methyl isobutyl ketone was removed therefrom with a rotary evaporator, to provide 25.5 g of 6-isopropyl-2-naphthol as precipitates in a yield of 57% based on 2,6-diisopropylnaphthalene.

The 6-isopropyl-2-naphthol obtained was found to have the following properties.

N.M.R. ($\delta$, $CDCl_3$): 1.3–2.4 (d, 6H), 2.9 (m, 1H), 3.7 (1H), 7.0–8.2 (m, 6H).
Purity: 99.6% (DSC)
Elemental Analysis: Calc. C, 83.8; H, 7.5; 0, 8.7; Found C, 83.6; H, 7.7, 0, 8.7).
m.p: 111.2°–111.8° C. (lit. 111.5°–112.5° C.)

EXAMPLE 9

An amount of 100.0 g of a 4.5% aqueous potassium hydroxide solution was used in place of the potassium acetate solution and otherwise in the same manner as Example 1, the reaction was carried out for 12 hours. The results are shown in Table 2.

COMPARATIVE EXAMPLE 3

Acetonitrile was not used, and otherwise in the same manner as Example 8, the reaction was carried out for 15 hours. The results are shown in Table 2.

COMPARATIVE EXAMPLE 4

9,10-Dihydroanthracene was not used, and otherwise in the same manner as Example 8, the reaction was carried out for 15 hours. The results are shown in Table 2.

COMPARATIVE EXAMPLE 5

Neither acetonitrile nor 9,10-dihydroanthracene was used, and otherwise in the same manner as Example 8, the reaction was carried out for 15 hours. The results are shown in Table 2.

EXAMPLE 10

An amount of 0.05 g of tetralin (1000 ppm based on 2,6-diisopropylnaphthalene) was used in place of 9,10-dihydroanthracene, and otherwise in the same manner as Example 8, the reaction was carried out for 12 hours. The results are shown in Table 2.

COMPARATIVE EXAMPLE 6

An amount of 5.0 g of 9,10-dihydroanthracene ($10^{-5}$ ppm based on 2,6-diisopropylnaphthalene) was used, and otherwise in the same manner as Example 8, the reaction was carried out for 12 hours. The results are shown in Table 2.

tion was carried out under the pressure for 12 hours while air was fed thereinto at a rate of 20 liters per hour.

After the completion of the reaction, 50.0 g of methyl isobutyl ketone was added to the reaction mixture to separate an organic layer from an aqueous layer which was found to have a pH of 3.8). The organic layer was diluted with methanol and analyzed by liquid chromatography. The results are shown in Table 3.

The organic layer was mixed with 50.0 g of a 10% sodium hydroxide solution and an organic layer was separated again. Water and methyl isobutyl ketone were removed from the organic layer with a rotary evaporator, and there was added to the residue methyl isobutyl ketone anew in amounts equal to the removed water and methyl isobutyl ketone. The resultant solution was fed together with acetone into a three necked 500 ml capacity Pyrex (registered trademark) flask containing diluted sulfuric acid over 3 hours at reflux temperatures, while simultaneously an acetone-diluted 60% hydrogen peroxide aqueous solution was fed into the flask over 3 hours. After the addition, the reaction was carried out for another 2 hours.

After the completion of the reaction, the reaction mixture was neutralized with a diluted aqueous sodium hydroxide solution, and then acetone and water were removed therefrom. Then an amount of 50 g of n-octane was added to the reaction mixture, and the methyl isobutyl ketone was removed therefrom with a rotary evaporator, to provide 24.0 g of 6-isopropyl-2-naphthol as precipitates in a yield of 55% based on 2,6-diisopropylnaphthalene.

TABLE 2

| | Amount of methylene Containing Aromatic Compound[1] (ppm)[2] | Amount of Acetonitrile (parts by wt.)[3] | Conversion of 2,6-diisopropyl-naphthalene (mole %) | Yield of Reaction Product (mole %) | | | | | Yield of 6-isopropyl-naphthol (mole %)[3] |
|---|---|---|---|---|---|---|---|---|---|
| | | | | DHP | HHP | DCA | MHP | MCA | |
| Example 8 | $10^3$ | 0.20 | 83.6 | 7.0 | 1.2 | 0.4 | 68.4 | 3.6 | 57 |
| Example 9 | 11 | 0.20 | 89.0 | 12.0 | 4.3 | 1.5 | 50.4 | 6.6 | 33 |
| Comparative 3 | 11 | 0 | 95.3 | 9.8 | 3.3 | 1.6 | 43.6 | 7.0 | — |
| Comparative 4 | 0 | 0.20 | 70.5 | 4.0 | 1.6 | 0.5 | 41.9 | 7.1 | — |
| Comparative 5 | 0 | 0 | 70.3 | 3.6 | 1.8 | 1.0 | 41.7 | 7.6 | — |
| Example 10 | $10^3$ | 0.20 | 81.0 | 5.9 | 1.0 | 0.3 | 61.0 | 4.5 | — |
| Comparative 6 | $10^5$ | 0.20 | 3.5 | 0.1 | tr. | tr. | 1.8 | 0.3 | — |
| Example 11 | $10^3$ | 0.02 | 90.6 | 8.6 | 3.5 | 1.6 | 47.5 | 7.0 | — |

Notes:
[1] 9,10-Dihydroanthracene was used in Examples 8, 9 and 11, and Comparative Examples 3 and 6; and tetralin in Example 10.
[2] Based on 2,6-diisopropylnaphthalene used.
[3] Based on 2,6-diisopropylnaphthalene used.

EXAMPLE 11

An amount of 1.0 g of acetonitrile (0.02 parts by weight per one part by weight of 2,6-diisopropylnaphthalene) was used, and otherwise in the same manner as Example 8, the reaction was carried out for 12 hours. The results are shown in Table 2.

EXAMPLE 12

In a 500 ml capacity autoclave made from SUS 21L provided with a stirrer, a cooling tube, a sampling opening, an inlet tube and a thermowell were placed 50.0 g of 2,6-diisopropylnaphthalene, 100.0 g of a 4.5% aqueous potassium solution, 10.0 g of acetonitrile (0.2 parts by weight per one part by weight of 2,6-diisopropylnaphthalene), 10.0 g of a 1% aqueous solution of $PdCl_2$ (40 ppm as palladium based on 2,6-diisopropylnaphthalene) and 0.20 g of azobiscyclohexane carbonitrile. The autoclave was heated to 100° C. in an oil bath, and was pressurized to 5 kg/cm²G with air, and then the oxida- The 6-isopropyl-2-naphthol obtained was found to have the following properties.

N.M.R. ($\delta$, $CDCl_3$): 1.3–2.4 (d, 6H), 2.9 (m, 1H), 3.7 (1H),
7.0–8.2 (m, 6H).
Purity: 99.5% (DSC)
Elemental Analysis: Calc. C, 83.8; H, 7.5; O, 8.7; Found C, 83.6; H, 7.7, O, 8.7).
m.p.: 111.3°–111.8° C. (lit. 111.5°–112.5° C.)

EXAMPLE 13

An amount of 100.0 g of a 4.5% aqueous sodium hydroxide solution was used in place of the potassium acetate solution, and otherwise in the same manner as Example 12, the reaction was carried out for 12 hours. The results are shown in Table 3.

COMPARATIVE EXAMPLE 7

Acetonitrile was not used, and otherwise in the same manner as Example 12, the reaction was carried out for 15 hours. The results are shown in Table 3.

COMPARATIVE EXAMPLE 8

Palladium chloride was not used, and otherwise in the same manner as Example 12, the reaction was carried out for 15 hours. The results are shown in Table 3.

COMPARATIVE EXAMPLE 9

Neither acetonitrile nor palladium chloride was used, and otherwise in the same manner as Example 12, the reaction was carried out for 15 hours. The results are shown in Table 3.

EXAMPLE 14

An amount of 10.0 g of an aqueous sulfuric acid solution containing 1% of $Pd(NO_3)_2$ (40 ppm as palladium based on 2,6-diisopropylnaphthalene) was used in place of $PdCl_2$, and otherwise in the same manner as Example 12, the reaction was carried out for 12 hours. The results are shown in Table 3.

EXAMPLE 15

An amount of 10.0 g of an aqueous sulfuric acid solution containing 1% of $PdCl_2$ (2 ppm as palladium on 2,6-diisopropylnaphthalene) was used, and otherwise in the same manner as Example 12, the reaction was carried out for 12 hours. The results are shown in Table 3.

EXAMPLE 16

An amount of 1.0 g of acetonitrile was used, and otherwise in the same manner as Example 12, the reaction was carried out for 12 hours. The results are shown in Table 3.

TABLE 3

| | Amount of Palladium Compound (ppm)[1] | Amount of Acetonitrile (parts by wt.)[1] | Conversion of 2,6-diisopropyl-naphthalene (mole %) | Yield of Reaction Product (mole %) | | | | | Yield of 6-isopropyl-naphthol (mole %)[2] |
|---|---|---|---|---|---|---|---|---|---|
| | | | | DHP | HHP | DCA | MHP | MCA | |
| Example 12 | 40 | 0.20 | 81.0 | 6.9 | 1.9 | 0.8 | 64.0 | 4.8 | 55 |
| Example 13 | 40 | 0.20 | 89.3 | 8.6 | 2.3 | 1.0 | 50.0 | 7.3 | 35 |
| Comparative 7 | 40 | 0 | 92.3 | 7.0 | 3.5 | 1.3 | 41.9 | 8.5 | — |
| Comparative 8 | 0 | 0.20 | 70.5 | 4.0 | 1.6 | 0.5 | 41.9 | 7.1 | — |
| Comparative 9 | 0 | 0 | 70.3 | 3.6 | 1.8 | 1.0 | 41.7 | 7.6 | — |
| Example 14 | 40 | 0.20 | 81.3 | 7.0 | 1.8 | 1.0 | 63.8 | 5.5 | — |
| Example 15 | 2 | 0.20 | 75.5 | 5.1 | 1.6 | 0.9 | 51.9 | 5.7 | — |
| Exampel 16 | 40 | 0.02 | 85.7 | 6.6 | 2.4 | 1.0 | 48.6 | 7.0 | — |

Notes:
[1]Based on 2,6-diisopropylnaphthalene used.
[2]Based on 2,6-diisopropylnaphthalene used.

What is claimed is:

1. A method of oxidizing secondary alkyl substituted naphthalenes with molecular oxygen in a liquid phase to hydroperoxides, carbinols or mixtures of these, which comprises: oxidizing the secondary alkyl substituted naphthalene in the presence of an aromatic hydrocarbon having a fused ring which contains at least one methylene group therein, and having from 9 to 14 carbon atoms, in amounts of not more than about 1000 ppm based on the secondary alkyl substituted naphthalene used.

2. The method as claimed in claim 1 wherein the oxidation reaction is carried out in the presence of a palladium catalyst soluble in the reaction mixture in amounts of not less than about 0.5 ppm based on the secondary alkyl substituted naphthalene used.

3. The method as claimed in claim 1 wherein the oxidation reaction is carried out at a pH of not less than about 7.

4. The method as claimed in claim 1 wherein the oxidation reaction is carried out at a pH of not less than about 12.

5. A process of producing isopropylnaphthols which comprises:
oxidizing diisopropylnaphthalenes with molecular oxygen in a liquid phase to diisopropylnaphthalene monohydroperoxides in the presence of (a) an organic polar compound in amounts of about 0.001–10 parts by weight per one part by weight of the diisopropylnaphthalene used and (b) an aromatic hydrocarbon having a fused ring which contains at least one methylene group therein, and having from 9 to 14 carbon atoms, in amounts of from about $10^{-4}$ parts by weight to about 0.005 parts by weight per one part by weight of the diisopropylnaphthalene used; and then,
acid-decomposing the diisopropylnaphthalene monohydroperoxide to the isopropylnaphthol.

6. The method as claimed in claim 5 wherein the oxidation reaction is carried out at a pH of about 3–11.

7. The method as claimed in claim 5 wherein the oxidation reaction is carried out at a pH of about 4–9.

8. The method as claimed in claim 5 wherein the acid decomposition is carried out in the presence of a water-insoluble dialkyl ketone and acetone added.

9. The method as claimed in claim 8 wherein the water-insoluble dialkyl ketone is methyl isobutyl ketone.

10. A process of producing isopropylnaphthols which comprises:
oxidizing diisopropylnaphthalenes with molecular oxygen in a liquid phase to diisopropylnaphthalene monohydroperoxides in the presence of (a) an organic polar compound in amounts of about 0.001–10 parts by weight per one part by weight of the diisopropylnaphthalene used and (b) a palladium catalyst soluble in a reaction mixture in amounts of not less than about 0.1 ppm as metallic palladium based on the diisopropylnaphthalene used; and then,
acid-decomposing the diisopropylnaphthalene monohydroperoxide to the isopropylnaphthol.

11. The method as claimed in claim 10 wherein the oxidation reaction is carried out at a pH of about 3–11.

12. The method as claimed in claim 10 wherein the oxidation reaction is carried out at a pH of about 4–9.

13. The method as claimed in claim 10 wherein the acid decomposition is carried out in the presence of a water-insoluble dialkyl ketone and acetone added.

14. The method as claimed in claim 10 wherein the water-insoluble dialkyl ketone is methyl isobutyl ketone.

15. The method of claim 1, wherein the secondary alkyl substituted naphthalene has one or two secondary alkyl groups with 3 or 4 carbon atoms.

16. The method of claim 1, wherein the secondary alkyl substituted naphthalene is an isopropylnaphthalene or diisopropylnaphthalene.

17. The method of claim 1, wherein the secondary alkyl substituted naphthalene is 2,6-diisopropylnaphthalene.

18. The method of claim 3, wherein said step of oxidizing the secondary alkyl substituted naphthalene in the presence of the aromatic hydrocarbon having the fused ring is carried out in the presence of an alkali metal compound or alkaline earth metal compound.

19. The method of claim 1, wherein the aromatic hydrocarbon having a fused ring has an indane structure or tetralin structure.

20. The method of claim 19, wherein the aromatic hydrocarbon having a fused ring is tetralin, 9,10-dihydroanthracene or fluorene.

21. The method of claim 1, wherein the amount of the aromatic hydrocarbon having a fused ring is from about 5 to 1000 ppm.

22. The method of claim 1, wherein the amount of the aromatic hydrocarbon having a fused ring is from about 10 to 500 ppm.

23. The method of claim 2, wherein the palladium catalyst is palladium chloride, palladium nitrate or palladium acetate.

24. The method of claim 2, wherein the amount of the palladium catalyst is from about 2 to about 1000 ppm, based on the secondary alkyl substituted naphthalene.

25. The method of claim 5, wherein the diisopropylnaphthalene comprises 2,6-diisopropylnaphthalene.

26. The method of claim 5, wherein the aromatic hydrocarbon having a fused ring has an indane structure or tetralin structure.

27. The method of claim 26, wherein the aromatic hydrocarbon having a fused ring is tetralin, 9,10-dihydroanthracene or fluorene.

28. The method of claim 5, wherein the amount of the aromatic hydrocarbon having the fused ring is from about $5 \times 10^{-4}$ to about 0.003 parts by weight, per part by weight of the diisopropylnaphthalene.

29. The process of claim 5, wherein the organic polar compound is an aliphatic or aromatic nitrile compound, an aliphatic or aromatic nitrated compound, a chlorinated benzene, dimethylsulfoxide or sulforane.

30. The method of claim 5, wherein the organic polar compound is acetonitrile, propionitrile, valeronitrile, benzonitrile, nitromethane, nitrobenzene, or dichlorobenzene.

31. The process of claim 5, wherein the organic polar compound is used in an amount of from about 0.1 to 5 parts by weight, per part by weight of the diisopropylnaphthalene.

32. The process of claim 31, wherein the organic polar compound is acetonitrile.

33. The method of claim 9, wherein the palladium catalyst is used in amount of about 10 to 50 ppm, as metallic palladium, based on the diisopropylnaphthalene.

* * * * *